United States Patent [19]

Barry

[11] Patent Number: 4,509,521
[45] Date of Patent: Apr. 9, 1985

[54] HEADACHE RELIEF METHOD

[76] Inventor: Terrence J. Barry, 6820 N. Augusta Dr., Hialeah, Fla. 33015

[21] Appl. No.: 462,350

[22] Filed: Jan. 31, 1983

[51] Int. Cl.³ .............................................. A61N 1/32
[52] U.S. Cl. .................................. 128/421; 128/419 C
[58] Field of Search ..................... 128/1 C, 421–423, 128/419 C

[56] References Cited

U.S. PATENT DOCUMENTS

| 3,388,699 | 6/1968 | Webb et al. | 128/1 C |
| 3,522,811 | 8/1970 | Schwartz et al. | 128/419 C |
| 3,650,277 | 3/1972 | Sjostrand et al. | 128/419 C |
| 4,014,347 | 3/1977 | Halleck et al. | 128/422 |
| 4,084,595 | 4/1978 | Miller | 128/422 |
| 4,121,594 | 10/1978 | Miller et al. | 128/422 |
| 4,147,171 | 4/1979 | Greene et al. | 128/421 |
| 4,155,366 | 5/1979 | DiMucci | 128/421 |
| 4,167,190 | 9/1979 | Sorenson et al. | 128/423 R |

FOREIGN PATENT DOCUMENTS

| 0061753 | 10/1982 | European Pat. Off. | 128/421 |
| 0627817 | 10/1978 | U.S.S.R. | 128/419 C |

Primary Examiner—William E. Kamm
Assistant Examiner—Mitchell J. Shein
Attorney, Agent, or Firm—Jack E. Dominik

[57] ABSTRACT

The present invention discloses human headache relief by application of electrical pulses of an approximate frequency of 10–12 pulses per second to a headache sufferer's skin. Ideally, the pulses are of an amplitude just below the sufferer's pain tolerance level (typically 60 to 150 volts) and are applied by two electrodes: a ground electrode makes contact with any skin area away from the neck or head and a live electrode makes contact with the sufferer's neck or head, depending on the type headache suffered. Further, the pulses preferably have a square wave form with the pulse width approximately 40 microseconds. An application for two minutes is normal and usually provides at least 6 hours relief.

7 Claims, 2 Drawing Figures

HEADACHE RELIEF METHOD

BACKGROUND OF INVENTION

This invention relates to a method for the relief of headaches and more particularly relates to use of electrical stimulation for elimination of extracranial headaches in humans.

SUMMARY OF THE PRIOR ART

It is well known that the application of electrical stimulation to the body of a human patient may produce therapeutic and anesthetizing affects, including the inducement of sleep. As described in U.S. Pat. No. 4,014,347 (Halleck et al.) pain may be suppressed by prolonged stimulation of the nerves involved in transmittal of the pain signals. To the same effect are U.S. Pat. Nos. 4,084,595 (Miller) and 4,121,594 (Miller et al). In U.S. Pat. No. 3,762,396 (Ballentine et al) sleep may be induced by application of electrical signals to a human sufferer's head, such signals to have frequencies associated with the human alpha brain wave and REM during sleep. Lastly, U.S. Pat. No. 3,791,373 (Winkler et al) discloses that a patient may be anesthetized by application of electrical current. The prior art devices have utilized various frequencies, including automatic scanning of frequencies during treatment, and various wave forms; these variations have frequently been claimed to have eliminated the side effects of such electrical treatment. Also various prior art devices have been designed with the object of minimizing the power consumed so that the device may be portable (i.e., operate on batteries) and of long-life between recharges. But none of these devices provides a cure for human headaches.

Greater than 90% of all headaches are: (1) headaches due to painful dilation and distention of cranial arteries; (2) headaches due to sustained contraction of skeletal muscle about the face, scalp and neck; or (3) headaches from diseases of the paranasal spaces ("sinus headaches"). Beeson, P. B., McDermott, W., Textbook of Medicine, 14th edition, page 616, W. B. Saunders Co., Philadelphia, 1975. But effective headache relief by the application of electrical stimulation to the body is not known in the prior art.

SUMMARY OF THE INVENTION

The present invention provides human headache relief by application of electrical pulses of an approximate frequency of 10–12 pulses per second to a headache sufferer's skin. Ideally, the pulses are of an amplitude just below the sufferer's pain tolerance level (typically 60 to 150 volts) and are applied by two electrodes: a ground electrode makes contact with any skin area away from the neck or head and a live electrode makes contact with the sufferer's neck or head, depending on the type headache suffered. Further, the pulses have a square wave form with the pulse width approximately 40 microseconds. An application for two minutes is normal and usually provides at least 6 hours relief.

BRIEF DESCRIPTION OF THE DRAWINGS

The accompanying drawings illustrate a preferred embodiment of the invention according to the best mode so far devised by the applicant, and in which.

DESCRIPTION OF THE PREFERRED EMBODIMENT

Figure 1:
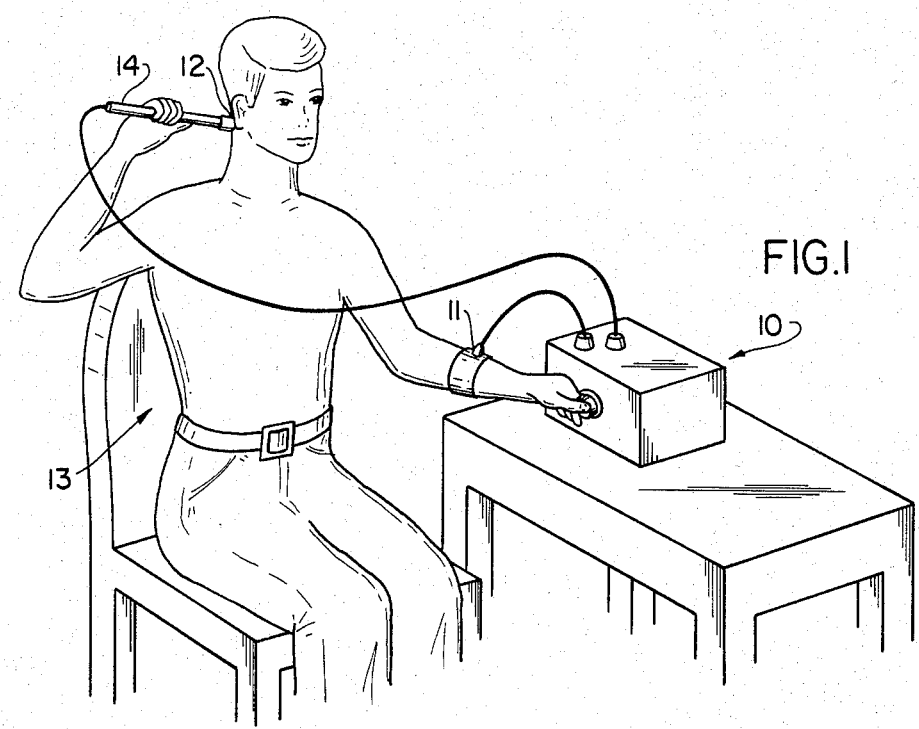
FIG. 1 is a view of a headache sufferer self administering the method.

The preferred embodiment of the inventive method to relieve a sufferer of a headache is to apply electrical pulses with the following characteristics:

Frequency: 11 pulses per second
Shape: square wave
Width: 40 microseconds
Amplitude: 50–200 volts (depends on the individual sufferer, points of contact, skin moisture, and pain threshold)

for a time period of two minutes to the sufferer's neck or head with a return ground attached to the sufferer's forearm, back or thigh. The pulse amplitude is empirically selected as described below and held constant during the application.

Tests conducted with patients who were suffering from headaches have shown that certain of the pulse parameters are critical for effective headache relief while others have some flexibility in allowing a degree of variation from patient to patient while still producing effective results in relieving the headache.

First, the pulse must have the characteristics of a square wave. Several other wave descriptions were not successful in providing relief.

Second, the pulse width or pulse duration may vary from 35–45 microseconds and still achieve positive results; however, the optimum width has been identified to be 40 microseconds. Deviation from that optimum width begins to deteriorate the effectiveness of the application to a point of being ineffective if the deviation is greater than 5 microseconds from the 40 microseconds optimum pulse width.

Third, the pulse rate may vary from 10–12 pulses per second and still achieve positive results; however, the optimum pulse rate has been identified as 11 pulses per second and any deviation from that pulse rate begins to deteriorate the effectiveness of the application to a point of being ineffective if the deviation is greater than a one pulse per second deviation from the 11 pulses per second optimum pulse rate.

Fourth, the applied pulse amplitude (peak voltage) is not critical in the narrow sense and will vary from patient to patient depending upon the patient's natural impedance and sensitivity to the discomfort associated with increased voltage application. The normal range of voltage applied generally runs from 50–150 volts, and in some exceptional cases, voltage application may go as high as 200 volts. With some patients, the "first time application" causes a degree of apprehension which will cause them to limit the peak voltage to about 60 volts on the first application. Familiarity with the process minimizes their apprehension and on subsequent applications they routinely will achieve a higher applied peak voltage. Positive results of headache relief have been routinely achieved throughout the 50–200 volt range with the norm, however, running in the 50 to 150 volt range.

Lastly, normal time duration for a successful application is two minutes at peak voltage acceptable to the patient. If the headache continues after the first two minute application (particularly if peak voltage was low), then a second two minute application normally resulted in abatement or total relief from the headache.

Applications longer than two two-minute applications have not been required in the patients treated.

FIG. 1 shows headache sufferer 13 connected to headache relief apparatus 10. The ground electrode 11 is shown placed on the sufferer's forearm, although positioning on the sufferer's thigh or back will produce approximately the same results. The live electrode 12 is shown placed on the back of the sufferer's neck, although placement on the forehead is preferable for sinus headaches, and other locations on the head have been successfully used in some patients. Electrode 12 may be covered with terry cloth and moistened so that when it is placed in contact with the sufferer's neck the insulative effect of the intervening hair can be overcome by the conductivity of the moisture from the terry cloth. Of course, the moistened terry cloth could be replaced by any other appropriate conductive medium. Also live electrode 12 may be attached to a handle 14 for easy manipulation—it it should be noted that due to the sufferer's hair and irregular body surface about the neck area some manipulation of the live electrode will be required to insure a good electrical contact. It is believed that any electrode size, shape, or material that produces a good electrical contact may be substituted for the particular electrode sizes, shapes, and materials disclosed without noticeable change in the results disclosed.

In operation, the sufferer himself or another individual places the two electrodes 11, 12 in contact with the patient as depicted in FIG. 1. The frequency of the pulses and the pulse width are not variable to the sufferer, so the only parameter to be determined is the pulse amplitude, (i.e. voltage). This insures easy and efficient use of the method because only one electrical adjustment is made and misleading adjustments made at frequencies and pulse widths differing from those of the treatment are avoided. The pulse amplitude for treatment is determined by increasing the amplitude from zero until the pain threshold of the sufferer is reached. Then the amplitude is adjusted so that it is approximately 90 to 95% of the amplitude at the pain threshold or just below the sufferer's maximum level of discomfort. The sufferer himself can most effectively make this adjustment as shown in FIG. 1.

As indicated in the examples to follow, the stimulation is continuous for two minutes, although the average sufferer's headache has been eliminated prior to this time.

It is believed that the method by which the invention relieves vascular headaches is as follows:

The electrical pulses are transmitted through the skin and subcutaneous tissues stimulating directly the arterial smooth muscle walls. The stimulation induces a segmental or generalized contractile response in the artery or arterials, thereby eliminating the cause of vascular headache pain. The arteries most commonly affected are the dural branches of the external carotid, temporal, post-auricular and occipital arteries.

It is believed that the method by which the invention relieves headaches caused by skeletal muscle contraction is as follows:

The electrical pulses are transmitted through the skin and subcutaneous tissues directly to the skeletal muscle tissue. The ground electrode frequently produces a clonic response in the skeletal muscle near its site of application. The active electrode only rarely produces a clonic response but alters the electrical state of the muscle toward a resting and refractile condition. Elimination of sustained contraction of the skeletal muscle thereby eliminates the cause of muscle contraction headache.

That other unknown factors are involved is evidenced by the prolonged effect (i.e. sustained headache relief) following discontinuation of the stimulus. This effect (sustained headache relief) following a brief electrical stimulation is in contrast to the prior art transcutaneous nerve stimulators which utilize prolonged stimulation with pain relief terminating on completion of nerve stimulation.

The present invention is in contrast to the prior art nerve stimulators which rely on mechanisms of blocking directly or indirectly afferent pain conducting nerves as opposed to actually relieving the cause of pain by direct effects on arteries and skeletal muscles.

The following examples illustrate the invention:

| Patient number | Applied pulse peak voltage | Duration of application | Results |
|---|---|---|---|
| A. | Approx. 60 volts | 2 Minutes | Cured for at least 6 hrs. |
| B. | Approx. 60 volts | 2 Minutes | Cured. The patient was subject to daily headaches Her headaches were absent for four days following treatment. |
| C. | Approx. 50 volts | 2 Minutes | 80% Cured. |
|  |  | 3 Minutes | 100% Cured for at least 6 hrs. |
| D. | Approx. 60 volts | 2 Minutes | Cured for at least 6 hrs. |
| E. | Approx. 70 volts | 2 Minutes | Cured for at least 6 hrs. |
| F. | Approx. 50 volts | 2 Minutes | Cured for at least 6 hrs. |

Figure 2:
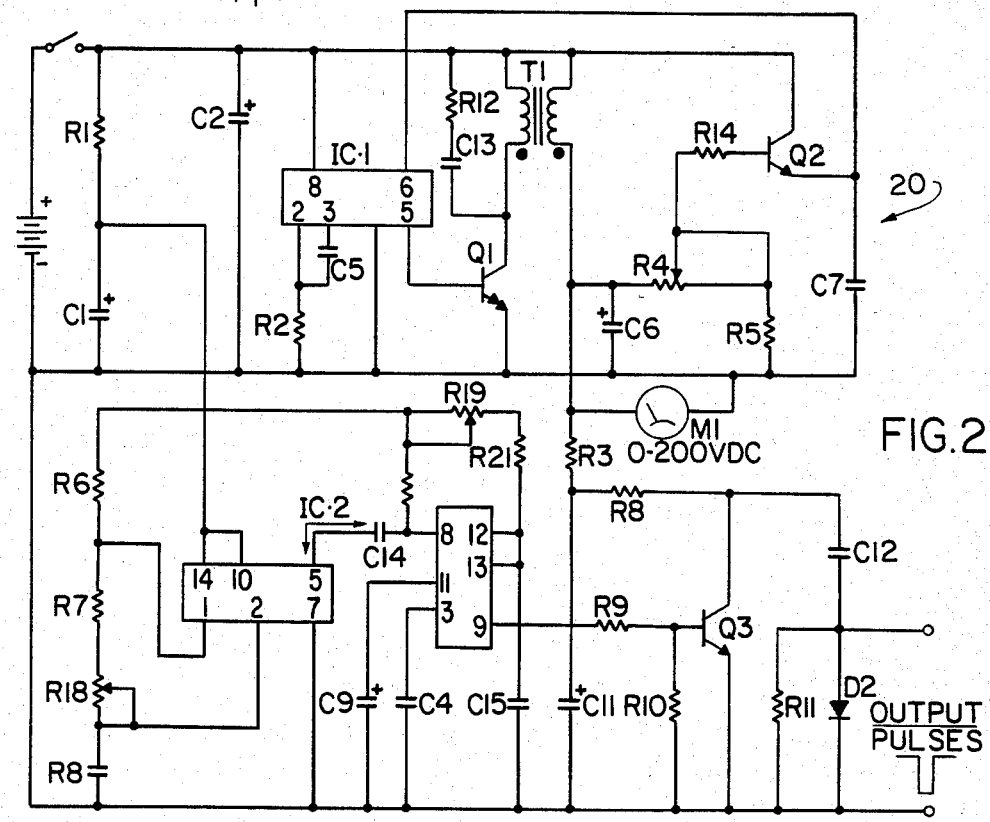
FIG. 2 is a schematic diagram of a typical device which generates electrical pulses usable with the method.

FIG. 2 shows a schematic for a device 20 which will generate pulses usable with the method. Device 20 outputs square waves with a frequency of 11 pulses per second (the frequency may be adjusted by potentiometer R18), pulse width of 40 microseconds (the pulse width may be adjusted by potentiometer R19), and an amplitude from 0 to 200 volts (the amplitude is adjusted by potentiometer R4). The various circuit elements of FIG. 2 are as follows (resistance in ohms and capacitance in microfarads):

| IC-1 | Multivibrator | MC 3380P |
|---|---|---|
| IC-2 | Timer | NE 556 |
| Q1 | Transistor | MJE-3300 |
| Q2 | Transistor | 2N 3391 |
| Q3 | Transistor | MJE-13005 |
| T1 | Transformer | 20 turn primary, 200 turn secondary |
| R1 | Resistor | 100 |
| R2 | Resistor | 1K |
| R3 | Resistor | 22K |
| R4 | Potentiometer | 1 M |
| R5 | Resistor | 27K |
| R6 | Resistor | 10K |
| R7 | Resistor | 120K |
| R8 | Resistor | 1K |
| R9 | Resistor | 100 |
| R10 | Resistor | 1K |
| R11 | Resistor | 22K |
| R12 | Resistor | 100 |
| R14 | Resistor | 680 |
| R18 | Potentiometer | 50K |
| R19 | Potentiometer | 100K |
| R20 | Resistor | 1K |

| | -continued | |
|---|---|---|
| R21 | Resistor | 270K |
| C1 | Capacitor | 100, 6 V |
| C2 | Capacitor | 500, 25 V |
| C4 | Capacitor | 2.2 |
| C5 | Capacitor | .047 |
| C6 | Capacitor | 2.2, 250 V |
| C7 | Capacitor | .01 |
| C8 | Capacitor | .47, 100 V |
| C9 | Capacitor | 2.2, 25 V |
| C11 | Capacitor | 4.7, 250 V |
| C12 | Capacitor | .1, 250 V |
| C13 | Capacitor | .02 |
| C14 | Capacitor | .01 |
| C15 | Capacitor | 100 pf |

Having described one specific preferred embodiment of the invention, I claim:

1. A method of relief for a headache sufferer comprising the step of applying electrical pulses from a ground electrode and a live electrode to said sufferer, said pulses characterized by:
   (a) a frequency in the range of from 10 to 12 pulses per second,
   (b) a pulse shape approximately square,
   (c) a pulse width between 35 and 45 microseconds,
   (d) an amplitude in the range of from somewhat below said sufferer's pain threshold to said pin threshold, and
   (e) said pulses being applied to the sufferer by placing the ground electrode on a body portion other than the neck or head and applying the live electrode to the sufferer's neck or head.

2. The method of claim 1, wherein said pulses are applied to said sufferer for a time period of 4 minutes or less.

3. The method of claim 1, wherein said pulses are applied to said sufferer for a time period of approximately 2 minutes.

4. The method of claim 1, wherein said pulse width is approximately equal 40 microseconds.

5. The method of claim 4, wherein said frequency is approximately equal 11 pulses per second.

6. The method of claim 5, wherein said pulses are applied to said sufferer for a time period of 4 minutes or less.

7. The method of claim 5, wherein said pulses are applied to said sufferer for a time period of approximately 2 minutes.

* * * * *